(12) United States Patent
Tuttle et al.

(10) Patent No.: US 7,261,740 B2
(45) Date of Patent: Aug. 28, 2007

(54) TIBIAL KNEE PROSTHESIS

(75) Inventors: David R. Tuttle, Memphis, TN (US); Vernon R. Hartdegen, Collierville, TN (US); Stephen E. White, Cordova, TN (US); Robert M. Fencl, Cordova, TN (US); Robert H. Schmidt, Ft. Worth, TX (US)

(73) Assignee: Wright Medical Technology, Inc., Arlington, TN (US)

( * ) Notice: Subject to any disclaimer, the term of this patent is extended or adjusted under 35 U.S.C. 154(b) by 603 days.

(21) Appl. No.: 10/696,459

(22) Filed: Oct. 29, 2003

(65) Prior Publication Data

US 2005/0096747 A1   May 5, 2005

(51) Int. Cl.
*A61F 2/38* (2006.01)
*A61F 2/30* (2006.01)

(52) U.S. Cl. .................................. 623/20.32
(58) Field of Classification Search .. 623/20.32–20.34, 623/20.14–20.15, 20.21–20.31
See application file for complete search history.

(56) References Cited

U.S. PATENT DOCUMENTS

| | | | |
|---|---|---|---|
| 3,816,855 A | 6/1974 | Saleh | |
| 4,634,444 A * | 1/1987 | Noiles | 623/20.27 |
| 4,759,767 A | 7/1988 | Lacey | |
| 4,963,152 A | 10/1990 | Hofmann | |
| 5,071,438 A | 12/1991 | Jones et al. | |
| 5,116,375 A | 5/1992 | Hofman | |
| 5,203,807 A | 4/1993 | Evans et al. | |
| 5,219,362 A * | 6/1993 | Tuke et al. | 623/20.31 |
| 5,236,461 A | 8/1993 | Forte | |
| 5,370,699 A | 12/1994 | Hood et al. | |
| 5,413,604 A | 5/1995 | Hodge | |
| 5,609,639 A | 3/1997 | Walker | |
| 5,824,102 A | 10/1998 | Buscayret | |

(Continued)

FOREIGN PATENT DOCUMENTS

EP   0420460 B1   11/1994

(Continued)

OTHER PUBLICATIONS

Nozaki, et al., Observations of Femoral Rollback in Cruciate-Retaining Knee Arthoplasty, Clin. Orthop. Rel. Res., 404:308-314 (2002).

(Continued)

*Primary Examiner*—Pedro Philogene (57) ABSTRACT

A knee prosthetic including a tibial component defining medial and lateral concavities shaped to receive medial and lateral femoral condyles of the femur. The concavities have first portions for contact with the condyles during normal knee flexion and second portions for contact with the condyles during deep, or high, knee flexion. The medial concavity can include a conforming boundary that encompasses at least the first and second portions, wherein an area inside the conforming boundary has a generally flat surface. The flat surface allows the medial femoral condyle to slide and rotate posteriorly during high knee flexion. The conforming boundary can have a generally triangular shape with an apex extending anteriorly and a relatively wider base extending posteriorly, wherein the apex includes the first portion and the base includes the second portion. The relatively wider base portion advantageously allows additional area for posteriorly directed articulating contact during high knee flexion.

27 Claims, 9 Drawing Sheets

U.S. PATENT DOCUMENTS

| | | | |
|---|---|---|---|
| 5,871,543 | A | 2/1999 | Hofman |
| 5,871,546 | A | 2/1999 | Colleran et al. |
| 5,879,394 | A | 3/1999 | Ashby et al. |
| 5,935,173 | A | 8/1999 | Roger et al. |
| 5,964,808 | A * | 10/1999 | Blaha et al. ............. 623/20.28 |
| 6,004,351 | A | 12/1999 | Tomita et al. |
| 6,013,103 | A | 1/2000 | Kaufman et al. |
| 6,039,764 | A | 3/2000 | Pottenger et al. |
| 6,053,945 | A | 4/2000 | O'Neil et al. |
| 6,056,779 | A * | 5/2000 | Noyer et al. ............. 623/20.32 |
| 6,068,658 | A | 5/2000 | Insall et al. |
| 6,074,425 | A * | 6/2000 | Pappas .................... 623/18.11 |
| 6,139,581 | A | 10/2000 | Engh et al. |
| 6,165,223 | A | 12/2000 | Metzger et al. |
| 6,210,444 | B1 | 4/2001 | Webster et al. |
| 6,210,445 | B1 | 4/2001 | Zawadzki |
| 6,217,618 | B1 | 4/2001 | Hileman |
| 6,319,283 | B1 | 11/2001 | Insall et al. |
| 6,344,059 | B1 | 2/2002 | Krakovits et al. |
| 6,379,388 | B1 | 4/2002 | Ensign et al. |
| 6,458,160 | B2 | 10/2002 | Biegun et al. |
| 6,475,241 | B2 | 11/2002 | Pappas |
| 6,485,519 | B2 | 11/2002 | Meyers et al. |
| 6,558,427 | B2 * | 5/2003 | Leclercq et al. ......... 623/20.33 |
| 2001/0034555 | A1 | 10/2001 | Pappas |
| 2002/0103541 | A1 | 8/2002 | Meyers et al. |
| 2002/0107576 | A1 | 8/2002 | Meyers et al. |
| 2002/0156535 | A1 | 10/2002 | Pappas |
| 2003/0009229 | A1 | 1/2003 | Pappas |
| 2003/0009230 | A1 | 1/2003 | Gundlapalli et al. |
| 2003/0055501 | A1 | 3/2003 | Fell et al. |
| 2003/0060882 | A1 | 3/2003 | Fell et al. |
| 2003/0060884 | A1 | 3/2003 | Fell et al. |
| 2003/0060885 | A1 | 3/2003 | Fell et al. |
| 2003/0060888 | A1 | 3/2003 | Fell et al. |
| 2003/0100953 | A1 | 5/2003 | Rosa et al. |

FOREIGN PATENT DOCUMENTS

| | | |
|---|---|---|
| EP | 0400045 B1 | 5/1995 |
| EP | 0522822 B1 | 12/1995 |
| EP | 0970667 A1 | 1/2000 |
| EP | 1018322 A1 | 7/2000 |
| EP | 1023881 A2 | 8/2000 |
| EP | 0634155 B1 | 10/2001 |
| EP | 0732092 B1 | 2/2002 |
| EP | 0809987 B1 | 10/2002 |
| EP | 0913134 B1 | 3/2003 |
| WO | WO89/06947 A1 | 8/1989 |
| WO | WO94/05212 A1 | 3/1994 |
| WO | WO97/30664 A1 | 8/1997 |
| WO | WO98/02116 A1 | 1/1998 |
| WO | WO98/20818 A1 | 5/1998 |

OTHER PUBLICATIONS

Whiteside, et al., Functional Medial Ligament Balancing in Total Knee Arthoplasty, Clin. Orthop. Rel. Res., 380:45-57 (2000).

Pagnano, et al., Flexion Instability After Primary Posterior Curciate Retaining Total Knee Arthroplasty, Clin. Orthop. Rel. Res., 356: 39-46 (1998).

Soudry, et al., Effects of Total Knee Replacement Design on Femoral-Tibial Contact Conditions, J. Arthroplasty, 1:35-45 (1986).

Piazza, et al., Posterior Tilting of the Tibial Component Decreases Femoral Rollback . . . , J. Orthop. Res., 16:264-270 (1998).

Matsuda, et al., Knee Stability in Posterior Cruciate Ligament Retaining Total Knee Arthroplasty, Clin. Orthop. Rel. Res., 366:169-173 (1999).

Stiehl, et al., The Cruciate Ligaments in Total Knee Arthroplasty, J. Arthroplasty, 15(5): 545-550 (2000).

Bergfeld, et al., The Effects of Tibial Rotation of Posterior Translation in Knees in Which the PCL Has Been Cut, J. Bone Joint Surg. 83-A:1339-43 (2001).

Mihalko, et al., PCL Effects on the Flexion Space in Total Knee Arthroplasty, Clin. Orthop. Rel. Res., 360:243-250 (1999).

Churchill, et al., The Influence of Femoral Rollback on Patellofemoral Contact Loads in Total Knee Arthroplasty, J. Arthroplasty, 16(7): 909-918 (2001).

Matsumoto, et al., Axis Location of Tibial Rotation and Its Change With Flexion Angle, Clin. Orthop. Rel. Res., 371:178-182 (2000).

Todo, et al., Anteroposterior and Rotational Movement of Femur During Knee Flexion, Clin. Orthop. Rel. Res., 362:162-170 (1999).

Dennis, et al., In Vivo Anteroposterior Femorotibial Translation of Total Knee Arthroplasty: A Multicenter Analysis, Clin. Orthop. Rel. Res., 356:47-57 (1998).

Hirsch, et al., THE PCL in Total Knee Surgery, Clin. Orthop. Rel. Res., 309:64-68 (1994).

Andriacchi, et al., The Influence of Total Knee-Replacement Design on Walking and Stair-Climbing, J. Bone Joint Surg. 64-A:1328-1335 (1982).

Walker, An In Vivi Kinematic Determination of the F/S 1000 Medial Pivot Knee (1997).

Stiehl, et al., Fluoroscopic Analysis of Kinematics After Posterior Cruciate Retaining Knee Arthroplasty, J. Bone Joint Surg. 77-B:884-889 (1995).

Kocmond, et al., Stability and Range of Motion of Insall-Burstein Condylar Prostheses, J. Arthroplasty, 10(3): 383-388 (1995).

Banks, et al., In Vivo Kinematics of Cruciate Retaining and Substituting Knee Arthroplasties, J. Arthroplasty, 1(3): 297-304 (1997).

Elias, et al., A Correlative Study of the Geometry and Anatomy of the Distal Femur, Clin. Orthop. Rel. Res., 260:98-103 (1990).

Mancinelli, The Instantaneous Axis of Rotation of the Human Knee Joint, Dissertation to the West Virginia University (1994).

Mahoney, et al., Posterior Cruciate Function Following Total Knee Arthroplast, J. Arthroplasty, 9(6): 569-578 (1994).

Sorger, et al., The PCL in Total Knee Arthroplasty, J. Arthroplasty, 12(8): 869-879 (1997).

Li, et al., Cruciate-Retaining and Cruciate-Substituting Total Knee Arthroplasty, J. Arthroplasty, 16(8) Suppl 1: 150-156 (2001).

Bertin, et al., In Vivo Determination of Posterior Femoral Rollback . . . , J. Arthroplasty, 17(8): 1040-1048 (2002).

Most, et al., Femoral Rollback After Cruciate-Retaining and Stabilizing Total Knee Arthroplasty, Clin. Orthop. Rel. Res., 410:101-113 (2003).

Takatsu, et al., The Function of Posterior Tilt of the Tibial Component . . . , Bull. Hosp. Joint Dis., 57(4): 195-201 (1998).

Kim, et al., Rollback in PCL-Retaining TKA, J. Arthroplasty, 12(5): 553-561 (1997).

Bellemans, et al., Fluoroscopic Analysis of the Kinematics of Deep Flexion in TKA, J. Bone Joint Surg., 84-B:50-53 (2002).

Blaha, et al., Kinematics of the Human Knee Using an Open Chain Cadaver Model, Clin. Orthop. Rel. Res., 410:25-34 (2003).

* cited by examiner

TIBIAL KNEE PROSTHESIS

BACKGROUND OF THE INVENTION

1. Field of the Invention

The present invention is generally related to the field of knee prosthetics and specifically related to the field of tibial trays capable of providing high knee flexion with and without retention of the posterior cruciate ligament.

2. Description of Related Art

In U.S. Pat. No. 5,964,808 (the '808 patent) and U.S. Pat. No. 6,013,103 (the '103 patent) which are hereby incorporated herein by reference in their entireties, the assignee of the present patent application (Wright Medical Technology, Inc., of Arlington, Tenn.) introduced a knee prosthetic capable of better imitating the complex biomechanics and kinematics of the normal human knee. The knee prosthetic described in the '808 and '103 patents has been, and continues to be, successful, especially at facilitating movement within the normal ranges of knee flexion.

Various scientific publications recognize that the kinematics of a normal, uninjured knee when subject to deep or high knee flexion can become very complex. See, e.g., Bellemans, et al., *Fluoroscopic Analysis of the Kinematics of Deep Flexion in Total Knee Arthroscopy*, J. Bone Joint Surgery [Br] 84-B:50–3 (2002). Deep knee flexion, as used herein and in the prior art, is the same as high knee flexion and refers to relative movement of the femur with respect to the tibia to an angle of about 90° or greater. Such complex knee kinematics can be difficult to replicate using conventional knee prosthetics which are primarily intended to address more normal ranges of knee flexion.

Another issue associated with the implantation of knee prosthetics is that in some instances a surgeon may elect to retain the posterior cruciate ligament (PCL) of the knee when implanting tibial and femoral components of the knee prosthesis. Generally, it is believed by some that sparing the PCL facilitates a return to normal knee kinematics. Several publications have examined the effects of such PCL-sparing surgeries on knee kinematics, and in particular, the effects of PCL-sparing on knee kinematics in deep or high flexion. See, e.g., Most, et al., *Femoral Rollback After Cruciate-Retaining and Stabilizing Total Knee Arthroplasty*, Clinical Ortho. & Related Research, No. 410, pp 101–113 (2003); Bertin, et al., *In vivo Determination of Posterior Femoral Rollback for Subjects Having a NexGen Posterior Cruciate-Retaining Total Knee Arthroplasty*, 17 J. of Arthroplasty 1040–1048 (2002); Guoan et al., *Cruciate-Retaining and Cruciate-Substituting Total Knee Arthroplasty*, 16 J. of Arthroplasty 150–156 (Supp. 2001); Sorger, et al., *The Posterior Cruciate Ligament in Total Knee Arthroplasty*, 12 J. of Arthroplasty 869–879 (1997); Stiehl, et al., *Fluoroscopic Analysis of Kinematics After Posterior Cruciate-Retaining Knee Arthroplasty*, J. Bone Joint Surgery [Br] 77-B: 884–889 (1995); Mahoney, et al., *Posterior Cruciate Function Following Total Knee Arthroplasty*, 9 J. of Arthroplasty 569–578 (1994). Regardless of the efficacy of sparing the PCL, its retention often increases the complexity of knee kinematics throughout the range of knee flexion. In particular, PCL retention can result in combined shifting and pivoting of the femur with respect to the tibia due to its exertion of a laterally directed force on the femur.

Different prosthetic devices have been developed to address the various issues associated with deep knee flexion. In one example, there are knee prosthetics in which the tibial tray rotates with respect to the tibia, by being mounted for rotation on its tibial base. In another example, there are knee prosthetics in which the tibial tray translates (or slides) with respect to the tibia, by being mounted for translation (sliding) on its tibial base. There are also knee prosthetics in which the tibial tray both rotates and translates with respect to the tibia, by being mounted for rotation and translation on its tibial base. Although these prosthetic devices provide one option to facilitate high knee flexion, they are relatively complex due to the required relative movement of the components with respect to their supporting bones.

Prosthetic devices have also been developed having a high anterior lip that allows for resection of the PCL, or protects the PCL in a PCL-sparing surgery. However, additional options for PCL sparing, especially prosthetics that also account for deep knee flexion, are still desirable.

Therefore, it would be advantageous to have a knee prosthesis that allows for more normal kinematic motion at higher or deeper flexion angles. In addition, it would be advantageous if such a prosthetic provided for retention of the PCL as is preferred by many surgeons.

OBJECTS OF THE INVENTION

It is an object of the present invention is to provide a tibial knee prosthesis that allows for complex, combined motion of the femur with respect to the tibia which is believed to be more consistent with the natural motion of knees in deep flexion and allows for retention of the PCL in knee replacement surgeries.

It is a further object of the present invention is to provide a tibial knee prosthesis that allows for posterior and lateral motion during deep knee flexion, or in PCL-spared knees.

These and other objects of the invention are achieved by a tibial knee prosthesis having a medial concavity with a generally triangular shaped area bounded by an area of conformity. An anterior peak of the triangular shaped area facilitates effective low knee flexion activity wherein the medial femoral condyle primarily rotates with respect to the tibia. A wider posterior base of the generally triangular shape facilitates freer motion in moderate to deep flexion, including laterally directed motion from the PCL and posterior sliding with respect to the tibia.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

The invention is an improvement to the prior art medial pivot knee described in commonly assigned U.S. Pat. Nos. 5,964,808 and 6,013,103. The knee prosthetics taught by these patents will now be briefly described herein for context with respect to the exemplary preferred embodiment.

Figure 1:
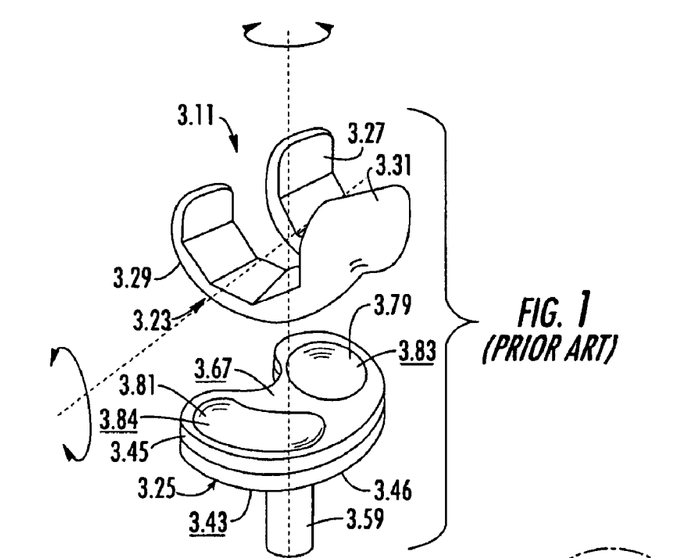
FIG. 1 is an exploded perspective view of a prior art right knee prosthesis.

The knee prosthesis 3.11 is designed to replace at least a portion of a knee joint 13 between a distal end 17 of a femur 15 and a proximal end 21 of a tibia 19, as shown in FIGS. 6–11. The femoral component 3.23 includes, in general, a medial condylar portion 3.27, a lateral condylar portion 3.29, and a patellar flange portion 3.31, as shown in FIG. 1. Reference should be made to the '103 patent for a complete and thorough understanding of the construction and function of the femoral component 3.23. It is possible, however, for the invention to be used with other femoral implants, including uni-compartmental femoral implants, or even with the patient's natural femur.

Figure 2:
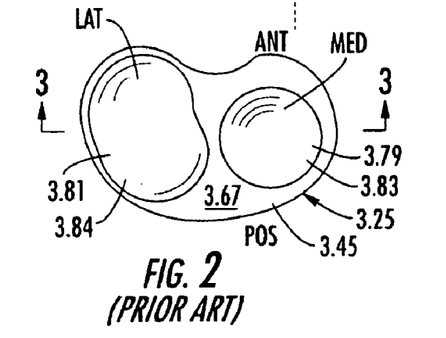
FIG. 2 is a top plan view of the tibial component of the prior art knee prosthesis of FIG. 1.

A tibial component 3.25 of the knee prosthesis 3.11 includes a base or tray member 3.43 for being secured to the proximal end 21 of the tibia 19, and an articular bearing, insert or superstructure member 3.45 for being fixedly mounted on the base member 3.43, as shown in FIG. 2.

Figure 3:
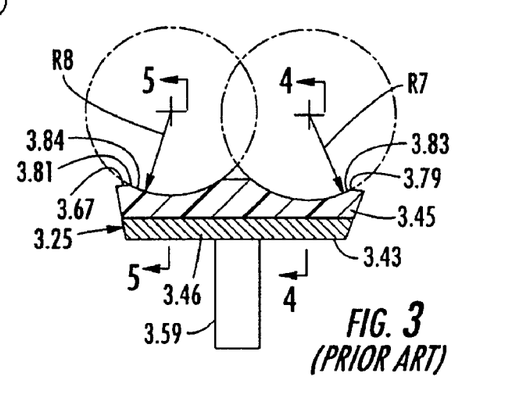
FIG. 3 is a sectional view substantially as taken on line 3—3 of FIG. 2, with portions thereof omitted for clarity.
Figure 4:
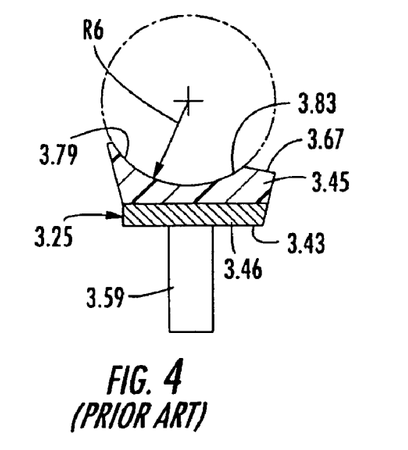
FIG. 4 is a sectional view substantially as taken on line 4—4 of FIG. 3, with portions thereof omitted for clarity.
Figure 5:
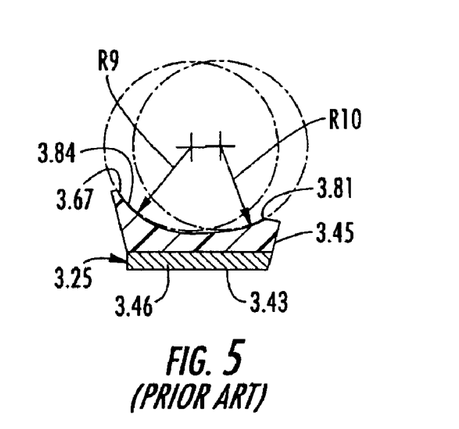
FIG. 5 is a sectional view substantially as taken on line 5—5 of FIG. 3, with portions thereof omitted for clarity.

The base member 3.43 preferably includes a head portion 3.46 and attachment aids 3.59 for helping to secure the head portion 3.46 to the proximal end 21 of the tibia 19, as shown in FIGS. 3–5. The attachment aids 3.59 may include one or more pegs, fins, screws, surface treatments, etc., on the lower surface of the head portion 3.46 as is apparent to those skilled in the art. In addition, the upper surface of the head portion 3.46 may include articular bearing attachment aids (not shown) for helping to fixedly secure the articular bearing member 3.45 to the base member 3.43. Such articular bearing attachment aids may include one or more undercut flanges extending upward from the upper surface of the head portion 3.46 for co-acting with co-acting grooves in the lower surface of the articular bearing 3.45 such as the attachment aids disclosed at column 2, lines 46–52 of the '808 patent.

The base or tibial tray member 3.43 can be constructed in various manners and out of various materials. Thus, for example, the base member 3.43 can be machined or molded from one or more material components.

Also as described in the '808 patent, the articular bearing member 3.45 has an upper or proximal surface 3.67 with a medial concavity 3.79 and a lateral concavity 3.81 for pivotally receiving and co-acting with the face surfaces of the respective medial and lateral condylar portions 3.27, 3.29 of the femoral component 3.23, as shown in FIG. 1. The articular bearing member 3.45 also has a lower or distal surface for being fixedly secured to the upper surface of the head portion 3.46 of the base member 3.43, as shown in FIGS. 3–5.

The medial concavity 3.79 has a face surface 3.83 for articulatingly receiving a portion of the face surface of the medial condylar portion 3.27 of the femoral component 3.23. The face surface 3.83 is preferably defined by a precise proximal sagittal curvature formed by the radius R6 shown in FIG. 4. In addition, a precise proximal coronal curvature is formed by the radius R7 shown in FIG. 3. The radius R6 is preferably the same size as the radius R7 so that the face surface 3.83 forms a semispherical shape.

Figure 6:
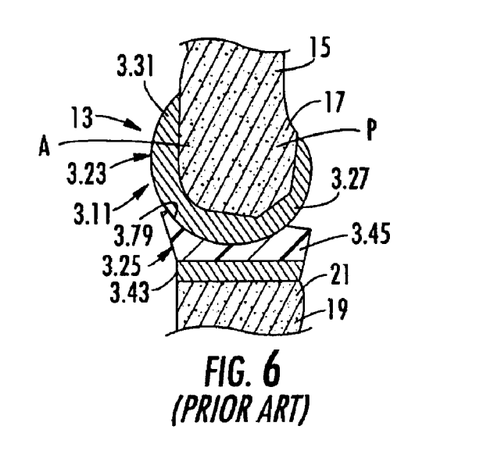
FIG. 6 is a somewhat diagrammatic medial sagittal sectional view of the prior art knee prosthesis of FIG. 1, shown implanted in a knee joint with the knee joint substantially fully extended.
Figure 8:
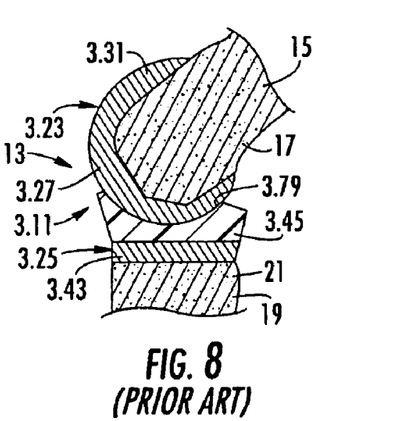
FIG. 8 is similar to FIG. 6 but shows the knee joint partially flexed.

In addition, the radii R6, R7 are preferably substantially congruent with or approximately the same size as the radii of the sagittal and coronal curvature of the medial femoral condyle 3.27 with appropriate clearances. In this manner, there can be substantially complete surface-to-surface contact between the face surface of the medial condylar portion 3.27 of the femoral component 3.23 and the face surface 3.83 of the medial concavity 3.79 of the tibial articular bearing member 3.45 throughout a significant portion of the range of flexion of the knee joint 13. This range of flexion, for example, may be between about full extension of the knee joint 13 (as shown in FIG. 6) and approximately 60° of flexion of the knee joint 13 (as shown in FIG. 8).

The lateral concavity 3.81 has a face surface 3.84 for articulatingly receiving a portion of the face surface of the lateral condylar portion 3.29 of the femoral component 3.23. The face surface 3.84 is preferably defined by a precise proximal coronal curvature formed by the radius R8 shown in FIG. 3, a precise anterior sagittal curvature formed by the radius R9 (as shown in FIG. 5) and a precise posterior sagittal curvature formed by the radius R10 (as also shown in FIG. 5).

Figure 7:
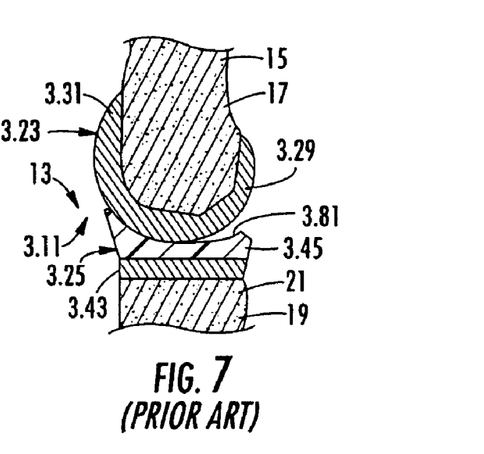
FIG. 7 is a somewhat diagrammatic lateral sagittal sectional view of the prior art knee prosthesis of FIG. 1, shown implanted in a knee joint with the knee joint substantially fully extended.
Figure 9:
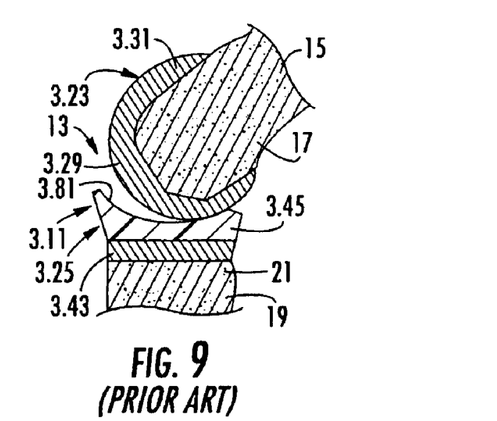
FIG. 9 is similar to FIG. 7 but shows the knee joint partially flexed.
Figure 10:
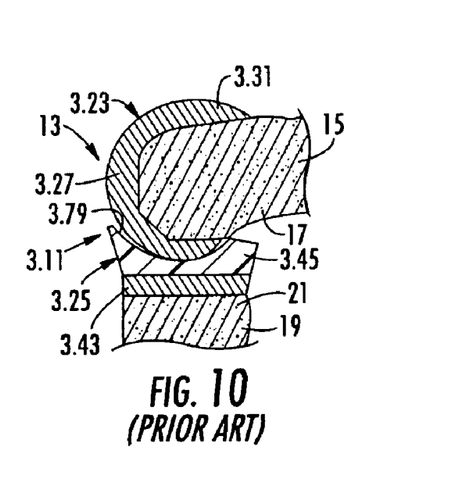
FIG. 10 is similar to FIG. 6 but shows the knee joint flexed substantially 90°.
Figure 11:
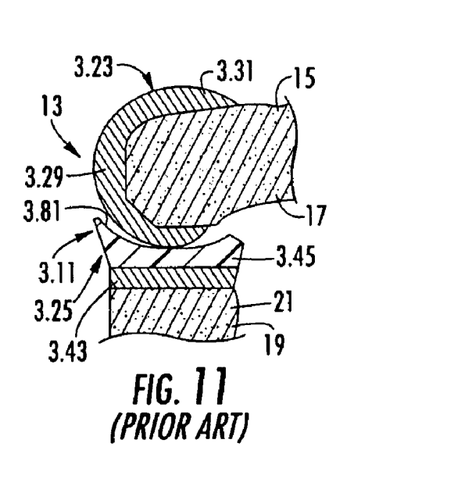
FIG. 11 is similar to FIG. 7 but shows the knee joint flexed substantially 90°.

The radii R8, R9, R10 are preferably substantially congruent with, or approximately the same size as, the radii as the lateral condyle with appropriate clearances. This substantial congruity promotes a substantial surface-to-surface contact between the face surface of the lateral condylar portion 3.29 of the femoral component 3.23 and the anterior end of the face surface 3.84 of the lateral concavity 3.81 of the tibial articular bearing member 3.45 during full extension of the knee joint 13, as shown in FIG. 7. There is preferably also substantial surface-to-surface contact between the face surface of the lateral condylar portion 3.29 of the femoral component 3.23 and the posterior end of the face surface 3.84 of the lateral concavity 3.81 of the tibial articular bearing member 3.45 during partial or greater extension of the knee joint 13, as shown in FIG. 9.

Figure 12A:
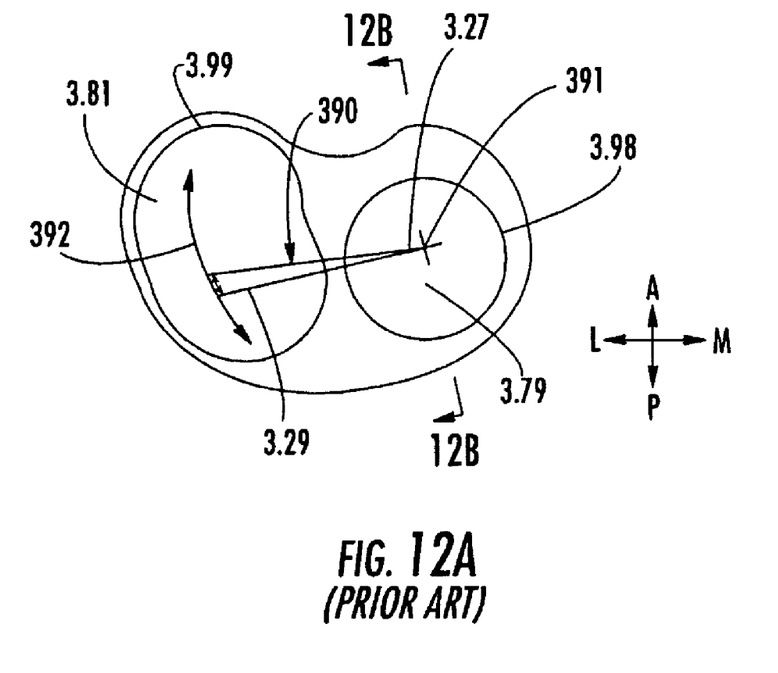
FIG. 12A depicts a general and schematic representation of the kinematics of the prior art medial pivot knee of FIGS. 1–11.
Figure 12B:
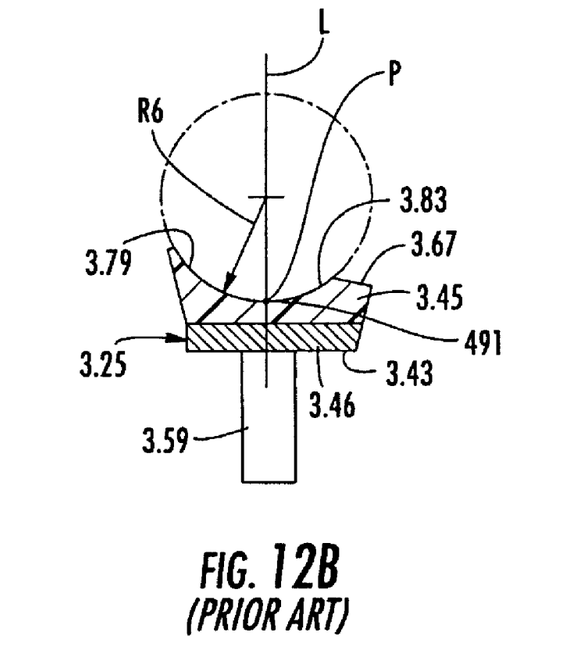
FIG. 12B depicts a view along line 12B—12B of FIG. 12A.

The lateral concavity 3.81 is preferably curved in a bean-like shape when viewed in plan (as shown in FIG. 2) so that during flexion of the knee joint 13, the femur 15 can rotate about a point 391 which is the most distal point within the medial concavity 3.79. As shown in FIG. 12B, the point 391 is at an intersection of a vertical line L extending in the proximal-distal direction and the surface defining the medial concavity. As is shown schematically in FIG. 12A, a medial-lateral axis extending through both the medial and lateral condyles represented by line 390 rotates about the point 391. This causes the lateral condylar portion of the femur (which is represented by the lateral end of the line 390) to swing about an arc 392 within the lateral concavity 3.81.

As previously mentioned, during deep flexion situations, the femur tends to posteriorly translate and rotate. This posterior translation and rotation can probably be equated (in terms of mechanics as opposed to directions) with the "combined spin and roll" motion previously recognized in studies of knee motion. See Blaha, et al., *Kinematics of the Human Knee Using an Open Chain Cadaver Model*, Clinical Ortho. & Related Research, No. 410, pp. 25–34 (2003) which is incorporated herein by reference.

By taking into account this better understanding of the biomechanics of the human knee, as understood by the current inventors, the present invention modifies the tibial prosthesis according to the '808 patent. These modifications allow the tibial prosthesis of the invention to better handle deep knee flex situations without the femur dislocating out of the tibial tray and accommodate those situations in which the PCL is retained. Generally, this is accomplished by modifying the medial concavity to have multiple conforming portions that can provide surface-to-surface contact between the medial femoral condyle and the medial concavity. These multiple conforming portions allow for sliding, rotation and other compound movements that are more consistent with the actual motion of a normal knee in deep or high flexion.

Figure 14:
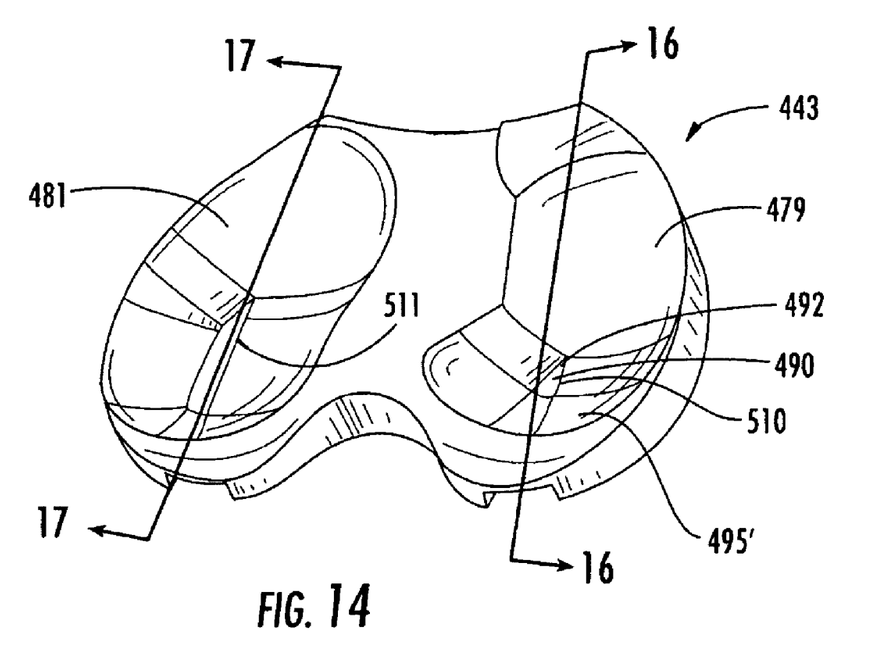
FIG. 14 is a perspective view of the tibial tray of FIG. 13A.

For example, as shown in FIG. 14, in one embodiment the present invention includes a tibial prosthetic or tray 443 that is an articular bearing member and includes a medial concavity 479 and a lateral concavity 481. The medial concavity 479 is shaped to receive and interact during knee articulation with a medial condyle, while the lateral concavity 481 is shaped to receive and interact with a lateral condyle. For instance, the concavities may receive and interact with the medial condyle 3.27 and the lateral condyle 3.29 of the femoral component 3.23 illustrated in FIG. 1. However, it should be noted that the tibial tray 443 is not limited to receiving the condyles of any particular type of femoral prosthesis and in fact could also interact with the condyles of a normal knee.

As is shown best in FIG. 14, the concavities 479, 481 are defined by raised and curved bearing surfaces upon which the femoral condyles 3.27, 3.29 can roll, slide, and pivot, or otherwise move in all degrees of freedom. However, it is strongly desirable that the condyles remain in contact (i.e., "conformity") with the concavities throughout the entire range of knee flexion, including deep flexion where knee dislocation in a normal knee is most likely to occur.

It should also be noted that although the tibial tray 443 in the illustrated embodiment is shown as being constructed of a unitary piece of material, it is also possible for the tibial tray to include multiple components. For instance, the tibial tray could include two separate trays, wherein each one of the trays defines a respective one of the concavities 479, 481. Tibial prostheses with two separate trays are typically known as unicompartmental knees as described, for example, in commonly assigned PCT publication WO 03/045256, which is hereby incorporated herein by reference. Also, the material used to construct the tibial tray 443 is preferably an ultra-high molecular weight polyethylene (UHMPE), but it could also be constructed of various metals, polymers, and other materials, singly or in combination and still fall within the purview of the present invention.

Figure 15:
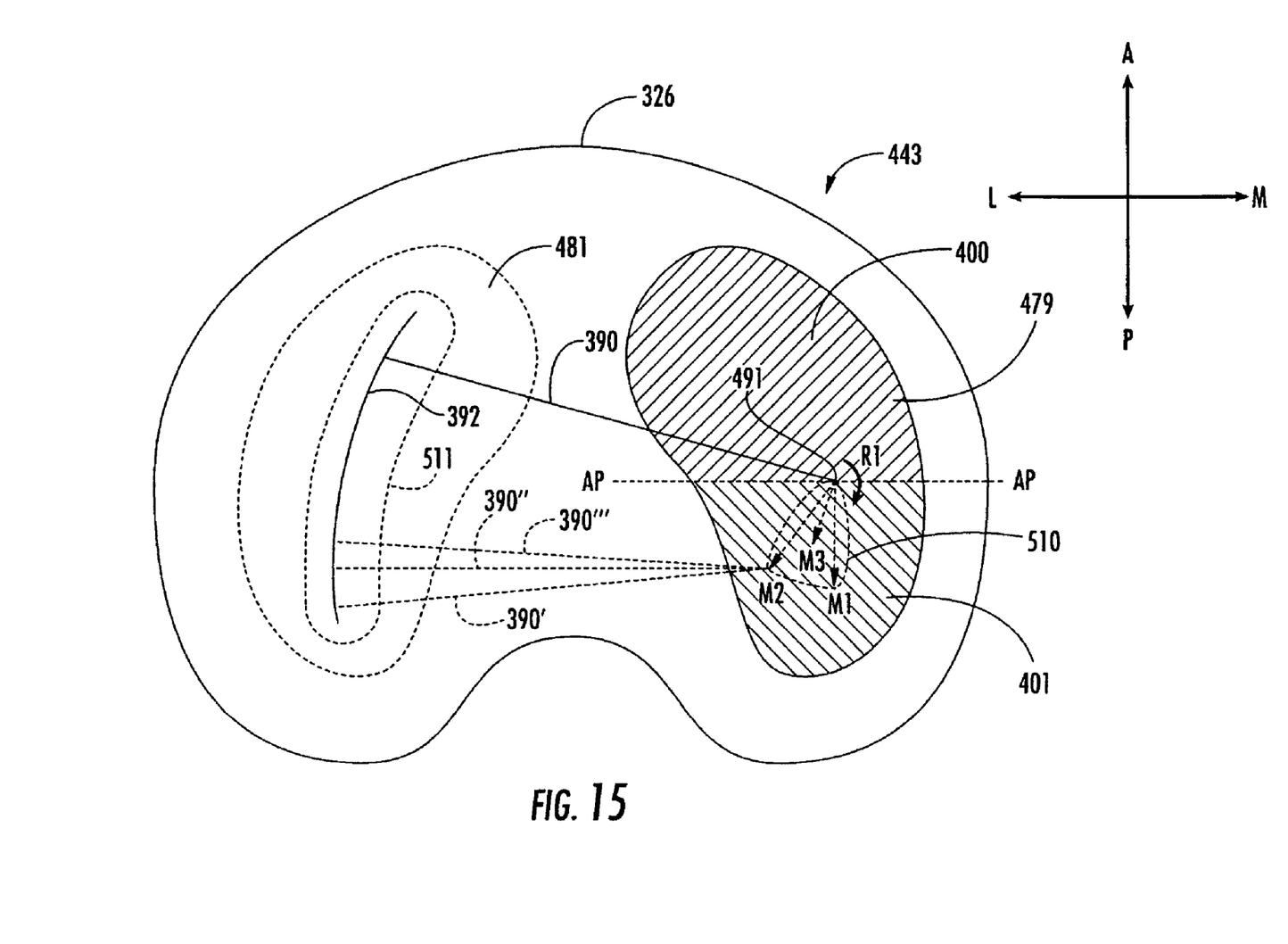
FIG. 15 is a schematic view of kinematics of the femur on the tibial tray of FIG. 13A.

For the purposes of the following discussion the term "anterior" is intended to mean pivot point 491 and all points anterior of the medial-lateral line AP—AP passing therethrough, as shown in FIG. 15.

As shown in FIG. 15, the medial concavity 479 of the tibial tray 443 includes a first portion 400 and a second portion 401 that engage the medial femoral condyle 3.27 during normal, and high, knee flexion, respectively. The first and second portions 400, 401 are most easily described in reference to modifications performed on the previously described, and preferably hemispherical, medial concavity 3.79 illustrated in the '808 patent. Generally, the first portion 400 is in the anterior portion of the medial concavity and interacts with the medial femoral condyle 3.27 during normal flexion. The second portion 401 is in the posterior area of medial concavity 479 of the tibial tray 443 and interacts with the medial femoral condyle 3.27 during high flexion and/or due to motion imparted on the femur by the PCL.

Figure 16:
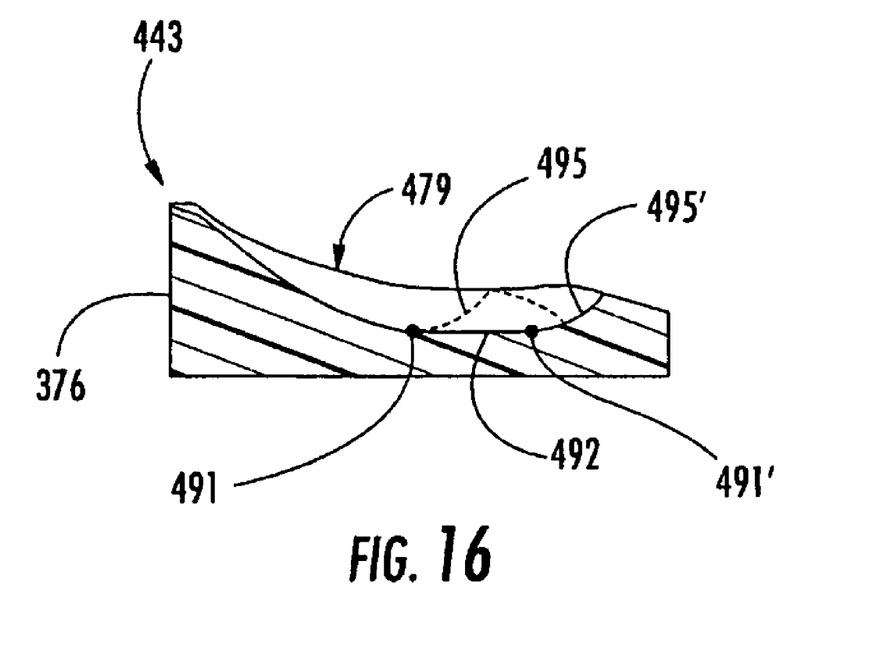
FIG. 16 is a sectional view of the medial concavity of the tibial tray shown in FIG. 13A.

In the embodiment illustrated in FIGS. 14 and 16, the aforementioned first portion 400 is defined as any portion of the medial concavity extending anteriorly from an imaginary line AP—AP passing medially-laterally through the pivot-only point 491. Generally, the first portion 400 of the tibial tray 443 corresponds, therefore, to the portion of the medial concavity of the tibial tray of the '808 patent which falls on and is anterior to pivot point 491.

The second portion 401 is generally defined as any portion of the medial concavity 479 other than the first portion. Specifically, this includes the portion of the medial concavity posterior to, but not including, the imaginary line AP—AP passing medially-laterally through the pivot-only point 491, as shown in FIG. 15. Despite the above-described preferred embodiment, it should be noted that the first and second portions could at least partially overlap, especially in the lateral concavity 481 during the application of external (e.g., muscle) forces where the posterior motion of the femur during high knee flexion is not as definite.

Even more specifically, the second portion is formed as follows. First, the posterior portion of the prior art medial concavity 3.79 is extended posteriorly (see FIG. 16). This is achieved by moving the pivot point 491, which as previously mentioned is also the lowest point in the medial concavity 3.79 of the '808 patent, posteriorly along a line perpendicular to the medial-lateral line AP—AP to point 491'. As a result, medial concavity now has a linear flat portion 492, as shown in FIGS. 14 and 16.

The entire posterior movement of pivot point 491 is foreseen as preferably being from 3 mm to 7 mm, or more preferably from 3 mm to 5 mm, or from 4 mm to 5 mm depending upon the size of the patient's knee. The various raised bearing surfaces surrounding the entire posterior portion of the medial concavity are also moved further posteriorly by approximately the same amount from point 495 where they would be in the medial concavity 3.79 of the '808 patent to point 495', as shown in FIG. 16.

The second portion of the medial concavity is also swept laterally at an angle. In the preferred embodiment, this is achieved by sweeping linear flat portion 492 at an arc of, for example, 30° in a lateral direction at a radius equal to the amount by which pivot point 491 was extended posteriorly. Of course other ranges of sweep could also be used such as 15°, 20°, 40°, 45°, or more, depending upon the amount of desired lateral movement. As shown in FIG. 15, this results in medial concavity 479 having a conforming area 510 whose boundary is not well defined (as will be described later) and containing a generally triangular shaped flat portion 490 of the illustrated embodiment. To account for the movement of the medial femoral condyle 3.27 into the medial portions of the generally triangular shaped flat portion 490, the original raised lateral bearing surface walls of the medial concavity 479 are moved laterally by an amount equal to the normal lateral motion of a medial condyle in high flexion while still taking into account the secondary design factors previously mentioned.

In the illustrated embodiment, the triangular shaped flat portion 490 preferably includes a peak and base portions which generally encompass or include portions the first and second portions, 400, 401, respectively. Referring again to FIG. 15, the peak portion extends generally in an anterior direction while the base includes the posterior two corners of the generally triangular shaped portion. One of the corners of the base extends laterally somewhat so as to allow lateral rotation of the medial femoral condyle 3.27 resulting from sparing of the PCL or deep flexion of the knee.

Figure 17:
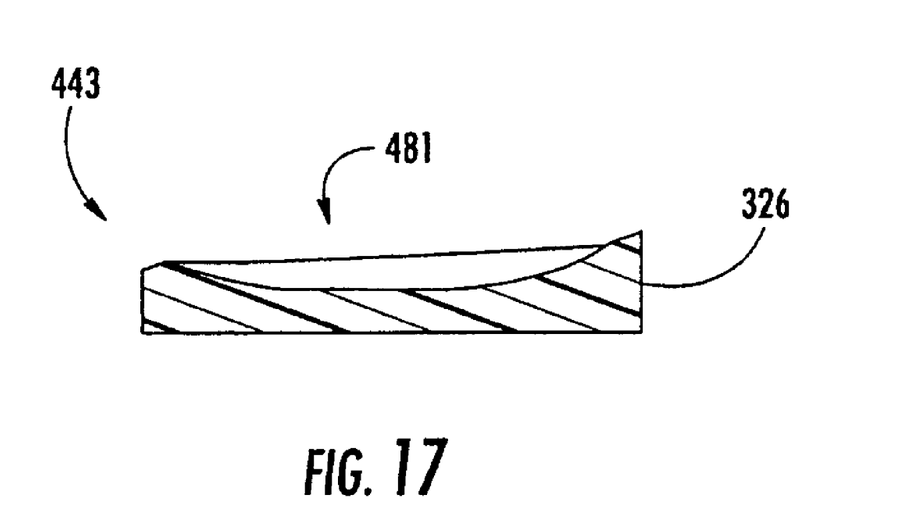
FIG. 17 is a sectional view of the lateral concavity of the tibial tray shown in FIG. 13A.

The lateral concavity 481 includes its own peripheral boundary 511 (as shown by a broken line in FIG. 15) which defines a modified portion of the lateral concavity 3.81 of the '808 patent. Generally, the peripheral boundary 511 is defined so as to ensure that there is no dislocation of the lateral condyle 3.29 out of the lateral concavity 481 due to the increased motion caused by the above-described modifications to the medial concavity 479, as shown by the peripheral boundary 510. Preferably, the area bounded by the peripheral boundary 511 is relatively flat to allow expanded sliding or rolling motion until the lateral condyle extends onto the upwardly curved surfaces surrounding the peripheral boundary, as shown in FIG. 17. Notably, it is preferred if both the medial and lateral condyles 3.27, 3.29 encounter the upwardly curved surfaces surrounding the boundaries 510, 511 in roughly the same position so that all of the restraint against dislocation is not provided by only one of the concavities 479, 481.

Figure 13A:
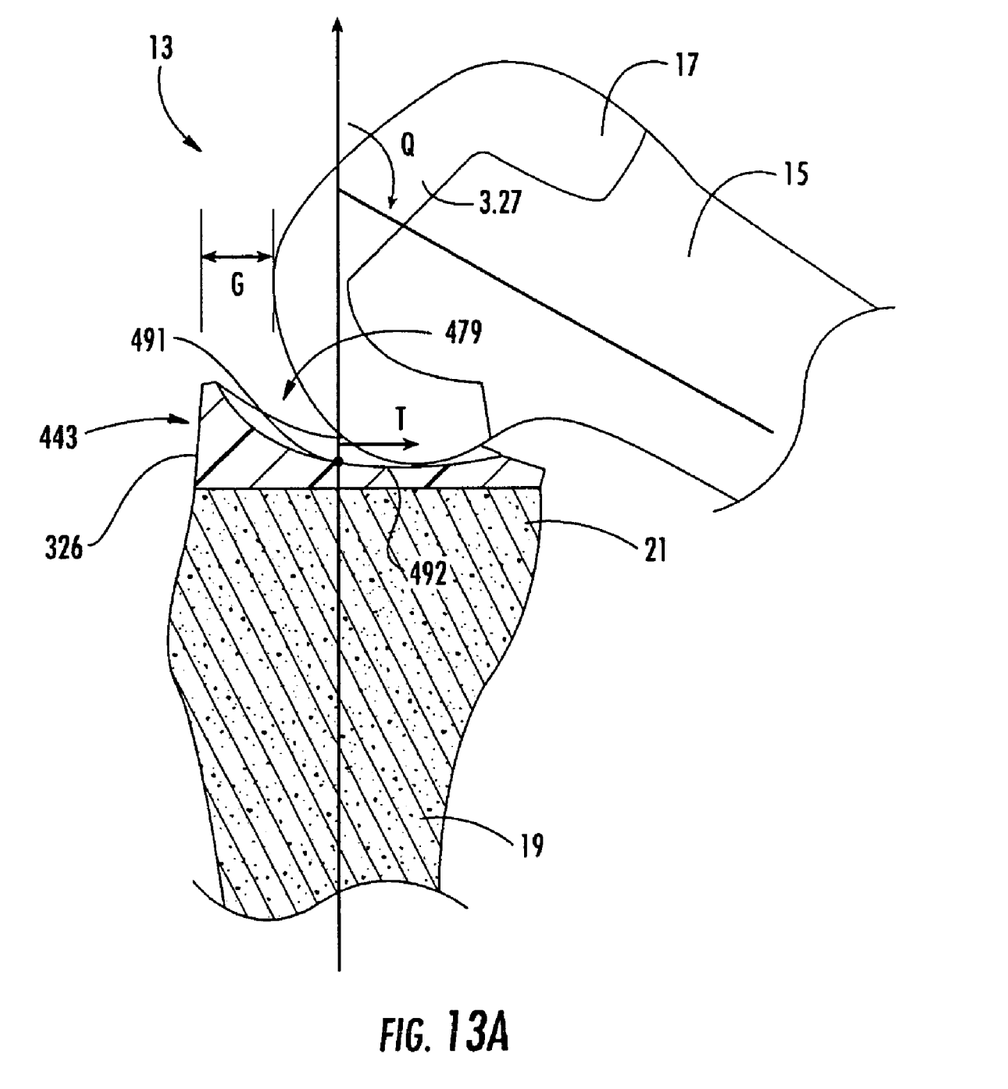
FIG. 13A is a sectional view of a medial concavity of a tibial tray of one embodiment of the present invention supporting a femur of a knee in deep flexion.

Without being wed to theory, it is believed that the above-described improvements to the tibial tray 443 result in relative tibial-femoral motion that is more consistent with normal knee kinematics throughout a full range of flexion than most conventional knee prosthetics without the complexity of a moving tibial tray. As shown in FIG. 13A, during deep flexion of the knee joint 13, the femur 15 is bent backwards greater than approximately 120° (angle Q) from tibia 19. As a result of this flexion, the entire femur 15 moves (translates) posteriorly in the direction of arrow T as allowed by the relatively flat surface within the peripheral boundary 510. This movement is symbolized by a resulting gap G between femoral condyles 3.27, 3.29 and an anterior lip 326 of the tibial tray 443.

Figure 13B:
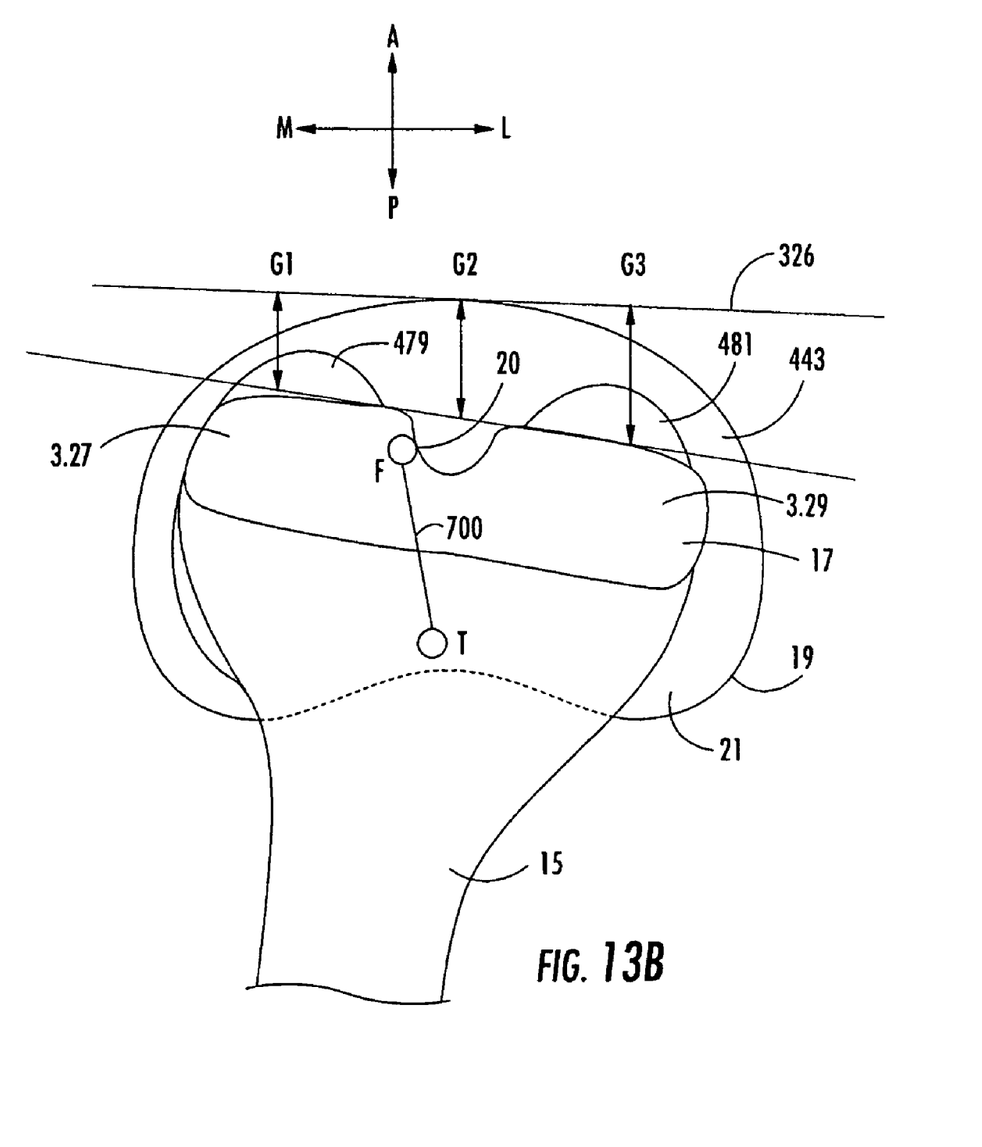
FIG. 13B is a plan view of the tibial tray of FIG. 13A supporting the femur.

This posterior translation, however, is not uniform in the medial-lateral direction due to rotation of the femur 15 with respect to the tibia 19, as shown in FIG. 13B. In particular, the gap G between the femoral condyles 3.27, 3.29 and the anterior lip 326 varies at a medial side G1, a middle portion G2, and a lateral side G3. In particular, the gap increases progressively from G1 to G2 and then G3 in the illustrated embodiment. This progressive increase in the gap G in the lateral direction is facilitated by the posteriorly directed expansion of the peripheral boundary 510 of the medial concavity 479 of the tibial tray 443 of the present invention.

The improvements of the tibial tray 445 of the present invention also allow for differences in motion caused by retention of the PCL. For instance, the PCL (represented schematically by a line 700 in FIG. 13B) is allowed by the present invention to further contribute to rotation of the femur 15 with respect to the tibia 19, as it would in a normal knee. The PCL 700 is connected to the posterior middle of the tibia 19 at one end, extends through an inter-condylar notch 20 of the distal femur 17, and then connects to the distal femur at its other end.

It should be noted that the PCL's connection to the distal femur 17 is offset somewhat in the medial direction due to its connection to the lateral side of the medial femoral condyle 3.29. Accordingly, this offset connection creates a natural tendency on the femur 15 as a whole to rotate in the lateral direction with respect to the tibia 19, even when the knee is not in flexion or deep flexion. The resulting lateral rotation of the PCL-sparing surgery is taken into account by the tibial tray 443 of the present invention, as described below.

Referring to FIG. 15, which are indicative of the kinematics of a knee using the tibial tray 443 of the present invention at particular moments in time, the result of high-flexion and forces from the PCL on the femur 15 is posterior translation and lateral rotation of the femur within the peripheral boundaries 510, 511. It should be noted that "rotation" of the femur 15 as described with respect to the present invention is not about a single stationary point as it is described with respect to the medial concavity of the tibial tray of the '808 patent. Rather, with the present invention, it is more likely that incremental rotation R1 of the medial condyle of the femur, as represented by the medial-lateral axis 390, occurs while the femur translates in directions indicated by arrows M1 and M2 (having lengths not necessarily to scale), as is also shown in FIG. 15.

Also as a result of the above-described compound motions allowed by the medial concavity 479 of the tibial tray 443 of the present invention, the kinematics of the knee joint 13 change when moving from normal flexion angles to deep or high flexion angles. For instance, when the knee joint 13 is an a normal flexion position, the medial condyle 3.27 only pivots about point 491 which remains stationary and is substantially identical in position to point 491 in the medial concavity 3.79 described in the '808 patent. Therefore, the knee joint 13 mimics medial pivot knee joint summarily described above and in the '808 patent in normal knee flexion. This is shown in FIG. 15 by the solid schematic version of femoral axis 390 and its associated solid lateral concavity arc 392.

When the knee joint 13 is bent towards deep flexion or the PCL acts upon the femur 15 (whether it is in deep flexion or not), the medial condyle 3.27 tends to translate posteriorly in direction M1 while simultaneously translating posteriorly and somewhat laterally in direction M2. In summation, this simultaneous translation may be represented as one movement in the direction of arrow M3. The general limits of the combined movements M1, M2, or M3 define the peripheral boundary 510 of the medial concavity 479.

The above-described compound motion of the femur 15 on its medial side causes a corresponding compound motion on its lateral side substantially surrounded by lateral peripheral boundary portion 511 contained within lateral concavity 481. Generally, in the illustrated embodiment of FIG. 15, the peripheral boundary 511 of the lateral concavity 481 is larger than peripheral boundary 510 of the medial concavity 479 so as to allow the lateral end of femoral axis 390 to take many angles and positions based upon a single position of the medial femoral condyle 3.27. For example, various changed positions of the femoral axis based upon a single position of the medial femoral condyle 3.27 are shown by broken lines 390', 390", and 390'''.

As previously noted, peripheral boundaries 510, 511 are not precisely defined or constrained by biomechanics, anatomy, surgical method, or manufacturing method, and therefore may vary or be varied depending upon these and other factors and still fall within the scope of the present invention. Accordingly, the peripheral boundaries 510, 511 are shown in the accompanying figures defined by broken lines. In fact, the present invention encompasses modification of the medial concavity 479 to allow a change in the position of the medial femoral condyle 3.27 on the tibial tray 443 when entering higher flexion, and/or retention of the PCL.

Therefore, although the embodiment of the present invention illustrated herein emulates one investigator's determination that deep or high knee flexion results in posterior and lateral movement of portion of the tibia on which the femoral condyles interact, different concepts and factors may also be applied and will still fall within the scope of the present invention. For instance, any tibial tray 445 design would be within the scope of the present invention as long as interaction constraint (conformity) between the medial femoral condyle 3.27 and the medial concavity 479 varies during high flexion.

Having described the structure of the invention, its operation will now be described. The tibial tray 443 is initially implanted into the body using conventionally known surgical techniques and instruments. Furthermore, because the tibial tray 443 is intended to be used in PCL retaining surgeries, the surgeon may opt to not dissect the PCL during implantation. As mentioned above, the surgeon may implant a range of femoral components, such as the femoral component 3.23 of the '808 patent, or may elect to not implant any femoral component.

During standing and relatively straight-legged activities where the femur is in-line with the tibia, the femoral condyles remain mainly in contact with the first portions 400 of the medial and lateral concavities 479, 481. Generally, in this mode, the tibial tray 443 of the present invention is operating in a manner similar to the tibial tray 3.43 described above and in the '808 patent.

Figure 18:
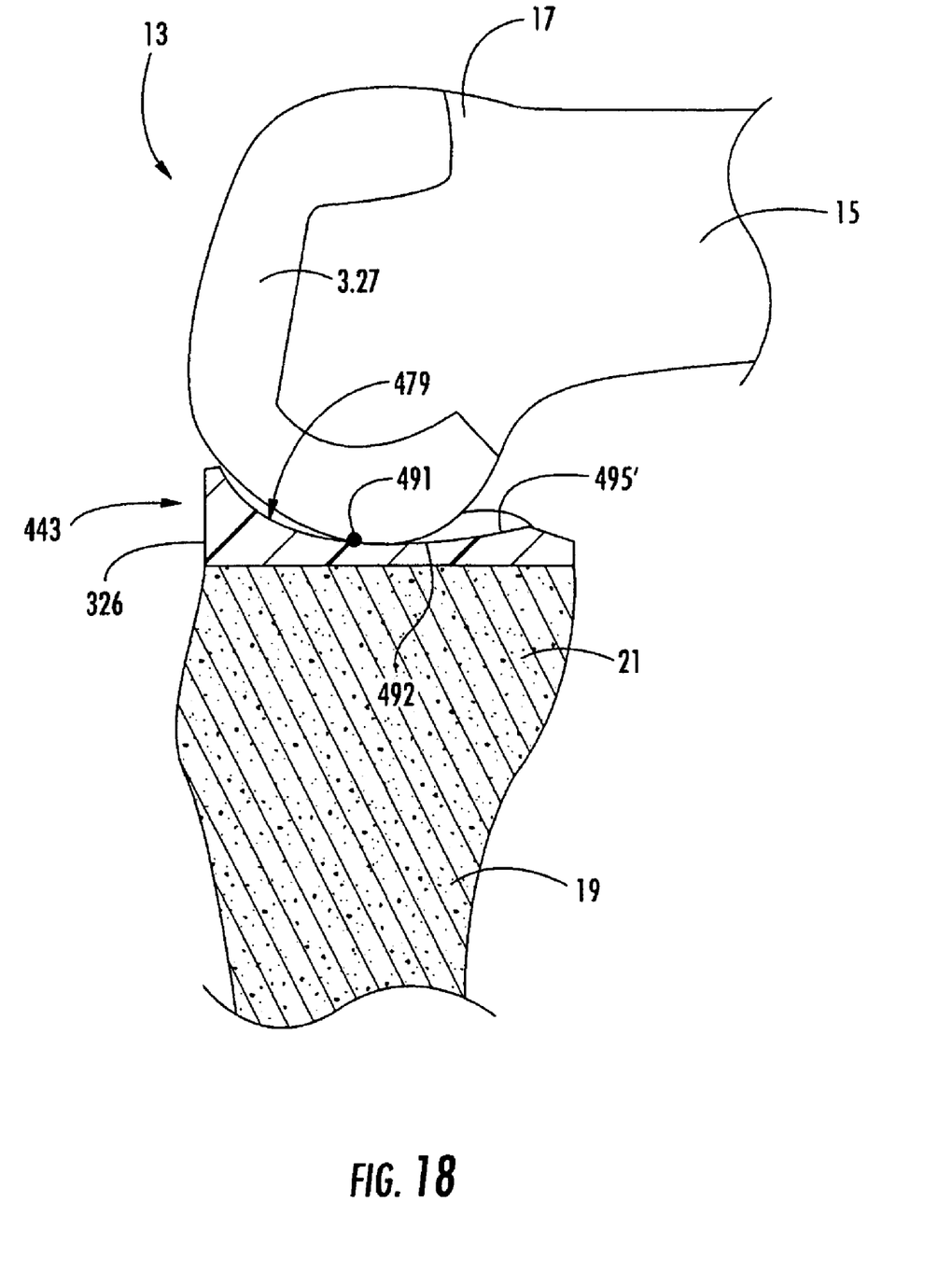
FIG. 18 is the knee of FIG. 13A in normal flexion.

Upon some normal-range flexion with action of the PCL, the femur 15 pivots about its sagittal axis and the medial condyle 3.27 begins to move posteriorly into the second portion 401 of the medial concavity 479, posterior of pivot point 491, as shown in FIG. 18. The lateral condyle 3.29 also moves into its respective second portion 401 as it follows the lead of the medial condyle 3.27 and the movement of the femur 15 as a whole. Generally, during this phase of movement, movement of the medial condyle 3.27 comprises sagittal pivoting and posterior translation only.

During deep flexion, or normal flexion but with the PCL acting upon the femur, the medial condyle 3.27 begins to move laterally and posteriorly, as shown in FIGS. 13A and 13B. The lateral condyle 3.29 moves and rotates even more as it follows the movement of the femur 15 as a whole, as shown schematically by FIG. 15. Once relatively deep flexion has been reached, the condyles 3.27, 3.29 are then constrained by the raised bearing surfaces within their respective concavities 479, 481 to prevent dislocation.

The present invention has many advantages. For instance, the use of first and second portions in the medial concavity 479 allows for complex, combined motion of the femur with respect to the tibia which is believed to be more consistent with the natural motion of knees in deep flexion and allows for retention of the PCL in knee replacement surgeries. In particular, the presence of posterior and lateral expansion of the medial concavity 479 as defined by the peripheral boundary 510 allows for posterior and lateral motion during deep knee flexion, or in PCL-spared knees. Further, the preferred embodiment's generally triangular shape of the peripheral boundary with an anterior peak facilitates the effective low knee flexion activity wherein the medial femoral condyle 3.27 primarily rotates. On the other hand, the wider posterior base of the generally triangular shape facilitates freer motion in moderate to deep flexion, including laterally directed motion from the PCL and posterior sliding.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A prosthetic for facilitating articulating contact of a tibia with a femur of a knee, said femur having a medial condyle and a lateral condyle, said knee prosthetic comprising:
    a tibial component defining a lateral concavity and a medial concavity;
    said lateral concavity having a first portion configured to interact with the lateral condyle of the femur during normal knee flexion and a second portion configured to interact with the lateral condyle of the femur during high knee flexion;
    said medial concavity having a first portion configured to interact with the medial condyle of the femur during normal knee flexion and a second portion configured to interact with the medial condyle of the femur during high knee flexion;
    wherein the lateral and medial concavities have different shapes and wherein the first and second portions are at least partially at separate locations within their respective concavities; and
    said medial concavity including a conforming boundary encompassing at least the first and second portions, a surface within the conforming boundary being generally flat, the conforming boundary having a progressively expanding medial-lateral width as it extends from an anterior end to a posterior end, and the conforming boundary having a generally triangular shape with an apex at the anterior end and a base at the posterior end.

2. A prosthetic of claim 1, wherein said tibial component includes a tibial tray that defines said medial and lateral concavities, said tibial tray being affixable to a proximal end of the tibia.

3. A prosthetic of claim 2, wherein said tibial component is constructed of a unitary piece of material.

4. A prosthetic of claim 1, wherein said first portion includes said apex and said second portion includes the remainder of said generally triangular shaped portion.

5. A prosthetic of claim 1, wherein said first portion includes said anterior end and said second portion includes the posterior end.

6. A prosthetic of claim 5, wherein the conforming boundary has an anterior-posterior length of at least 3 mm.

7. A prosthetic of claim 5, wherein the conforming boundary has an anterior-posterior length from 3 mm to 5 mm.

8. A prosthetic of claim 1, wherein said medial condyle can move within an area in which for any given position of the medial condyle, the lateral condyle can have many positions.

9. A knee prosthetic for facilitating movement of a knee through a large range of knee flexion angles, including high knee flexion, said knee prosthetic comprising:
 a femoral component having a medial condyle and a lateral condyle; and
 a tibial component defining a medial concavity and a lateral concavity;
  wherein the lateral concavity has a different shape than the medial concavity;
 wherein said medial and lateral concavities have first portions that are in articulating contact with the medial and lateral condyles of the femoral component during normal knee flexion;
  wherein said medial and lateral concavities have second portions that are at least partially separate from the first portions and are in articulating contact with the medial and lateral condyles of the femoral component during high knee flexion; and
 said medial concavity including a conforming boundary, an area within the conforming boundary having a generally flat surface, the conforming boundary having a generally triangular shape with an apex at the anterior end and a base at the posterior end.

10. A knee prosthetic of claim 9, wherein the tibial component is rigidly mounted to a tibia of the knee.

11. A knee prosthetic of claim 10, wherein the tibial component is adapted to allow preservation of a posterior cruciate ligament of the knee when attached to the tibia.

12. A knee prosthetic of claim 9, wherein said first portion includes said apex and said second portion includes the remainder of the area within the conforming boundary.

13. A knee prosthetic of claim 9, wherein said first portion includes said anterior end and said second portion includes the posterior end.

14. A knee prosthetic of claim 13, wherein the conforming boundary has an anterior-posterior length of at least 3 mm.

15. A knee prosthetic of claim 13, wherein the conforming boundary has an anterior-posterior length from 3 mm to 5 mm.

16. A knee prosthetic of claim 9, wherein said medial condyle can move within an area in which for any given position of the medial condyle, the lateral condyle can have many positions.

17. A prosthetic for facilitating articulating contact of a tibia with a femur of a knee, said femur having a medial condyle and a lateral condyle, said knee prosthetic comprising:
 a tibial component defining a lateral concavity and a medial concavity;
 said lateral concavity having a first portion configured to interact with the lateral condyle of the femur during normal knee flexion and a second portion configured to interact with the lateral condyle of the femur during high knee flexion; and
 said medial concavity having a first portion configured to interact with the medial condyle of the femur during normal knee flexion and a second portion configured to interact with the medial condyle of the femur during high knee flexion, said medial concavity having a generally triangular portion, said generally triangular portior having a generally flat contour, a peak of said generally triangular portion positioned anteriorly of a base of said generally triangular portion, and said generally triangular portion positioned to facilitate posterior and lateral translation of an articulation pivot point with the medial condyle of the femur during high knee flexion.

18. A prosthetic of claim 17, wherein a lateral corner of said base of said generally triangular portion extends laterally so as to allow lateral rotation of the medial femoral condyle in said generally triangular portion.

19. A prosthetic of claim 17, wherein said peak of said generally triangular portion has an angle of between about 15 degrees to about 45 degrees.

20. A prosthetic of claim 17, wherein said peak of said generally triangular portion has an angle of about 30 degrees.

21. A prosthetic of claim 17, wherein in normal knee flexion, said articulation pivot point with the medial femoral condyle is located substantially at said peak of said generally triangular portion.

22. A prosthetic of claim 17, wherein said first portion of said medial concavity includes said apex and said second portion of said medial concavity includes a remainder of said generally triangular portion.

23. A prosthetic for facilitating articulating contact of a tibta with a femur of a knee, said femur having a medial condyle and a lateral condyle, said knee prosthetic comprising:
 a tibial component defining a lateral concavity and a medial concavity;
  said medial concavity having a generally triangular portion, said generally triangular portion having a generally flat contour, a peak of said generally triangular portion positioned anteriorly of a base of said generally triangular portion, and said generally triangular portion positioned to facilitate posterior and lateral translation of an articulation pivot point with the medial condyle of the femur during high knee flexion.

24. A prosthetic of claim 23, wherein a lateral corner of said base of said generally triangular portion extends laterally so as to allow lateral rotation of the medial femoral condyle in said generally triangular portion.

25. A prosthetic of claim 23, wherein said peak of said generally triangular portion has an angle of between about 15 degrees to about 45 degrees.

26. A prosthetic of claim 23, wherein said peak of said generally triangular portion has an angle of about 30 degrees.

27. A prosthetic of claim 23, wherein in normal knee flexion, said articulation pivot point with the medial femoral condyle is located substantially at said peak of said generally triangular portion.

* * * * *